United States Patent [19]

Heine et al.

[11] 4,216,172
[45] Aug. 5, 1980

[54] PREPARATION OF CYCLOBUTANONES

[75] Inventors: Hans-Georg Heine; Willy Hartmann, Krefeld, both of Fed. Rep. of Germany

[73] Assignee: Bayer Aktiengesellschaft, Leverkusen, Fed. Rep. of Germany

[21] Appl. No.: 886,229

[22] Filed: Mar. 13, 1978

[30] Foreign Application Priority Data

Apr. 6, 1977 [DE] Fed. Rep. of Germany ....... 2715336

[51] Int. Cl.² ...................... C07C 45/00; C07C 45/02
[52] U.S. Cl. .................................... 568/364; 260/464; 260/465 D; 260/465 E; 260/465 F; 260/465 G; 260/465 H; 260/465 K; 260/557 R; 260/557 B; 260/558 R; 260/559 R; 560/37; 560/45; 560/48; 560/51; 560/53; 560/54; 560/55; 560/56; 560/59; 560/61; 560/62; 560/64; 560/65; 560/118; 560/119; 560/123
[58] Field of Search ............... 260/586 R, 590 C, 464, 260/465 F, 465 G, 465 H, 586 G, 586 F, 465 D, 465 E, 465 K, 557 R, 557 B, 558 R, 559 R; 560/566 A, 24, 25, 53, 54, 115, 116, 51, 123, 118, 119, 37, 45, 48, 55, 56, 59, 61, 62, 64, 65

[56] References Cited

U.S. PATENT DOCUMENTS

| | | | |
|---|---|---|---|
| 3,078,306 | 2/1963 | von Schickl et al. | 260/566 A |
| 3,129,248 | 4/1964 | England | 260/586 R |
| 3,408,398 | 10/1968 | Martin | 260/586 R |
| 4,028,418 | 6/1977 | van den Brink et al. | 260/586 R |

OTHER PUBLICATIONS

Marchand-Brynaert et al., "J.A.C.S.", vol. 94:8 (1972), p. 2870.
Hoonaert et al., "Angew Chem.", 87, Jahn. 1975, Nr. 15, pp. 552-553.
Sidani et al., "Angew Chem.", 86, Jahn. 1974, Nr. 7, p. 272.
Echngsfeld et al., "Angew Chem.", 72, Jahn. 1960, Nr. 22, pp. 836-843.
Ghosey et al., "Angew Chem.", 81 Jahn. 1969, Nr. 12, p. 468.
Seebach, "Meth. du Org. Chem.", Houber Weyl, vol. 4/4, pp. 180-202 (1971).

Primary Examiner—Norman Morgenstern
Attorney, Agent, or Firm—Sprung, Felfe, Horn, Lynch & Kramer

[57] ABSTRACT

A process for the preparation of a cyclobutanone of the formula

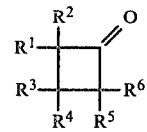

in which
$R^1$ to $R^6$ each independently is a hydrogen, halogen, cyano, alkoxy, alkoxycarbonyl, carboxamido, dialkylphosphono, alkyl, cycloalkyl, aryl, aralkyl or alkenyl radical, or two of them together with the carbon atom to which each is linked form a ring, comprising reacting an N,N-disubstituted carboxylic acid amide of the formula

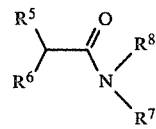

in which
$R^7$ and $R^8$ each independently is an alkyl, cycloalkyl, alkenyl, aryl or aralkyl radical or together form a ring, with an inorganic acid halide, and then reacting the product with a tertiary amine, an olefin of the formula

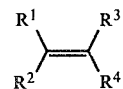

and a Lewis acid, and subsequently hydrolyzing the mass. Preferably isobutyric acid dimethylamide is employed as the carboxylic acid amide, phosgene is employed as the inorganic acid halide, triethylamine is employed as the tertiary amine and zinc chloride or titanium tetrachloride is employed as the Lewis acid. The products are known intermediates for insecticides.

18 Claims, No Drawings

PREPARATION OF CYCLOBUTANONES

The present invention relates to an unobvious process for the preparation of certain four-membered cyclic ketones.

It is known to prepare four-membered cyclic ketones from ketenes and olefins or alkynes (see D. Seebach in Houben-Weyl, Methoden der Organischen Chemie (Methods of Organic Chemistry), volume 4/4, G. Thieme, Stuttgart 1971).

This process can be carried out in the form of numerous variants (see, for example, loc. cit. page 185), but is restricted by the following points.

(1) The readiness of the ketenes to undergo cycloaddition onto, for example, an olefin, greatly depends on the substitution of the olefin. Thus, enamines and enol ethers react with dimethylketene many times more rapidly than unsubstituted olefins olefins halogenated at the double bond undergo virtually no cycloaddition.

(2) Ketenes dimerize readily. This process can compete successfully with the desired cycloaddition.

(3) In the presence of oxygen, ketenes very readily form peroxides, the presence of which in crude reaction mixtures can give rise to uncontrollable side reactions.

Furthermore, it is known (J. Am. Chem. Soc. 94, 2870 (1972), Angew. Chem. 86, 272 (1974) and Angew. Chem. 87, 552 (1975)) to prepare four-membered cyclic ketones from α-chloroenamines, silver tetrafluoroborate or zinc chloride, and olefins or alkynes and by subsequent hydrolysis. Some of the aforesaid disadvantages of ketene additions onto olefins and alkynes (cyclodimerization and peroxide formation) are overcome by this process. However, this cycloaddition also has deficiencies; thus, the α-chloroenamines required as starting compounds are tedious to prepare and, as a result of their sensitivity towards hydrolysis, can frequently only be isolated by wasteful processes. As is known (Angew. Chem. 81, 468 (1969)), α-chloroenamines are obtained, by dehydrohalogenation, from the amide chlorides available by reacting N,N-disubstituted carboxylic acid amides with inorganic acid halides. The amide chlorides tend to dimerize readily under catalysis by heat and bases (Angew. Chem. 72, 836 (1960) and DAS (German Published Specification) 1,080,760) unless at least one and, in general, two substituents are present in the α-position. Limits are therefore placed on variation of the substituents: for example, the 1-chloro-1-dialkylamino-ethylene equivalent to the ketene is hitherto unknown.

In contrast even to the most reactive ketenes, α-chloroenamines surprisingly react completely with deactivated olefins under mild reaction conditions to give the corresponding cyclo-adducts. Thus, 1-chloro-1-dimethylamino-2-methyl-prop-1-ene adds smoothly onto 1,1-dichlorobutadiene at 20°–30° C. in methylene chloride and in the presence of zinc chloride in the course of a few hours. Hydrolysis of the cyclo-adduct gives 2,2-dimethyl-3-(β,β-dichlorovinyl)-cyclobutanone, in 80% yield, the bromination and subsequent treatment with aqueous sodium hydroxide solution of which quantitatively gives permethric acid (2,2-dimethyl-3-(β,β-dichlorovinyl)-cyclopropanecarboxylic acid), which is essential for the preparation of numerous insecticides of the pyrethrum type. U.S. Patent Application Ser. No. 827,515, filed Aug. 24, 1977, now pending relates to these process steps. However, they are carried out individually and the intermediate products are isolated in each case. This is not ideal, especially from the point of view of industrial feasibility.

There is therefore an interest in providing a process, which can easily be carried out industrially, for converting N,N-disubstituted carboxylic acid amides into α-chloroenamines, via the particular amide chlorides and dehydrohalogenation thereof, and further reaction of the products with olefins to give four-membered cyclic ketones.

The present invention now provides a process for the preparation of a four-membered cyclic ketone of the general formula

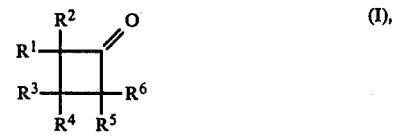

in which
$R^1$–$R^6$, which are selected independently of one another, each denote alkyl, cycloalkyl, aryl, aralkyl, alkenyl or alkynyl, any of which may be optionally substituted, or hydrogen, cyano, alkoxy, alkoxycarbonyl, carboxamido or dialkylphosphono, and $R^1$ and $R^2$ and/or $R^3$ and $R^4$ and/or $R^5$ and $R^6$, or $R^1$ and $R^3$ and/or $R^2$ and $R^4$ and/or $R^5$ and $R^6$, with the atoms to which they are linked, can form an optionally substituted ring, in which an N,N-disubstituted carboxylic acid amide of the general formula

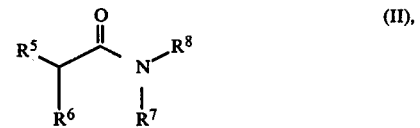

in which
$R^5$ and $R^6$ have the above-mentioned meanings,
$R^7$ and $R^8$, which may be identical or different, each represent optionally substituted alkyl, cycloalkyl, alkenyl, aryl or aralkyl, or $R^7$ and $R^8$, with the atoms to which they are linked, form an optionally substituted ring, is reacted with an inorganic acid halide, preferably phosgene or thionyl chloride, and the product (the corresponding amide halide) is then reacted with a tertiary amine, an olefin of the general formula

in which
$R^1$–$R^4$ have the above-mentioned meanings,
and a Lewis acid and subsequently hydrolyzed.

In the process according to the invention, the product mixture obtained by treating an N,N-disubstituted carboxylic acid amide with an inorganic acid halide and subsequently with a tertiary amine is reacted with an olefin in the presence of a Lewis acid. Although Lewis acids react with amine hydrochlorides and in some cases react exothermically with tertiary amines—the Lewis acid, which is necessary for the reaction with the α-chloroenamine formed in situ, thus becomes bonded thereto—the cyclo-addition nevertheless proceeds successfully and in unexpectedly high yields.

These results are surprising and open up new possibilities of also using cyclo-additions with reactive α-chloroenamines for the preparation of four-membered cyclic ketones industrially, starting from readily available and cheap starting compounds.

The process according to the invention can be described as a sequence of four component steps which can be carried out without isolating the intermediate products thereby formed.

COMPONENT STEP A:

In component step A, a carboxylic acid amide of the general formula (II), optionally in a diluent (which term includes a solvent), for example diethyl ether, chloroform, toluene, methylene chloride, chlorobenzene, tetrahydrofuran, dibutyl ether, benzene, 1,2-dichloroethane, 1,1,2,2-tetrachloroethane, carbon tetrachloride, acetonitrile, cyclohexane or petroleum ether, is reacted with an inorganic acid halide in a manner which is in itself known from the literature (supra) in a temperature range from about $-10°$ C. to $100°$ C., preferably about $-10°$ C. to $40°$ C.

Suitable inorganic acid halides are, for example, thionyl chloride, phosgene, phosphorus pentachloride, thionyl bromide and phosphorus trichloride; phosgene is particularly preferred.

The reaction is carried out, for example, by initially introducing the carboxylic acid amide and optionally a diluent into a stirred vessel and adding the inorganic acid halide, preferably phosgene or thionyl chloride, in portions, while cooling or at a moderately elevated temperature. The inorganic acid halide is preferably used here in an amount at least equimolar to that of the carboxylic acid amide. About 1.1 to 1.3 molar equivalents of acid halide are sometimes employed in the reaction.

In some cases, depending on the solvent and the carboxylic acid amide of the general formula (II) employed, a crystalline addition compound forms during or after the addition of the inorganic acid halide.

Component step B (see below) can be carried out when the addition of the inorganic acid halide has ended. However, it is frequently appropriate to first stir the mixture further for some time at room temperature and to remove any unreacted inorganic acid halide, for example by distillation, optionally under reduced pressure.

In a further process variant, the inorganic acid halide, in a suitable diluent, is initially introduced and the carboxylic acid amide is added in portions, while cooling or at a moderately elevated temperature. The molar ratio indicated above is also maintained in this process variant.

A number of carboxylic acid amides of the general formula (II) can be used as starting compounds for the process according to the invention. Examples which may be mentioned are carboxylic acid amides which are derived from the following carboxylic acids: isobutyric acid, acetic acid, propionic acid, isovaleric acid, butyric acid, caproic acid, lauric acid, stearic acid, isovaleric acid, chloroacetic acid, phenylacetic acid, α-ethylbutyric acid, α-methylbutyric acid, adipic acid, adipic acid monoethyl ester, β,β-dimethylbutyric acid, cyclohexanecarboxylic acid, cyclohexylacetic acid, cyclobutylacetic acid, cyclopentanecarboxylic acid, cyclobutanecarboxylic acid and ω-chlorocaproic acid.

Suitable amine components for these carboxylic acid amides are, inter alia, dimethylamine, diethylamine, dibutylamine, methylethylamine, diisobutylamine, dicyclohexylamine, piperidine, pyrrolidine, morpholine, methylbenzylamine and dibenzylamine.

Dimethylamides, in particular isobutyric acid dimethylamide, are preferably used as amides of the general formula (II).

COMPONENT STEP B:

In component step B, the carboxylic acid amide of the general formula (II), which has been reacted with an inorganic acid halide according to component step A, optionally in one of the diluents listed, is dehydrohalogenated with a basic agent, for example a tertiary amine, and optionally in the presence of a Lewis acid, in a temperature range from about $-30°$ C. to $100°$ C., preferably about $-20°$ C. to $40°$ C.

The dehydrohalogenation is carried out, for example, by reacting the reaction mixture, obtained according to component step A, with the tertiary amine in portions in the same reaction vessel, while cooling or at room temperature ($20°$ C.). The amine is used in at least the stoichiometric amount, appropriately in a slight excess. When the addition of the amine has ended, component step C (see below) is carried out with the resulting reaction mixture.

However, it can also be appropriate to stir the reaction mixture further for some time under the dehydrohalogenation conditions, optionally even at a moderately elevated temperature, and only then to proceed according to component step C.

A further process variant consists in first reacting the reaction product, obtained according to component step A, with about 1 to 1.3 molar equivalents of a Lewis acid while cooling, and then adding the tertiary amine incrementally.

A further process variant consists in separating off the hydrochloride formed from the reaction mixture obtained during the reaction according to component step B before carrying out component step C.

Examples of Lewis acids which can be used are: zinc chloride, titanium tetrachloride, aluminum chloride, zinc bromide, iron(III) chloride, tin(II) chloride and tin(IV) chloride, i.e. polyvalent metal chlorides and bromides are preferred.

Inorganic or organic bases can be employed as tertiary amines which can be used for the dehydrohalogenation. Tertiary organic amines, for example trimethylamine, triethylamine, dimethylaniline, pyridine, quinoline, tributylamine, dicyclohexylmethylamine and dimethylbenzylamine, are preferably used.

COMPONENT STEP C:

In component step C, the reaction mixture obtained according to component step B is reacted with an olefin of the general formula (III). For this, it is necessary to convert the dehydrohalogenation product present in the reaction mixture into a reactive form. This can be effected by reacting the dehydrohalogenation product with, for example, silver tetrafluoroborate. Other salts, such as, for example, silver hexafluorophosphate, silver perchlorate and silver hexafluoroarsenate, can also be used. However, the Lewis acids indicated above, especially zinc chloride or titanium tetrachloride, are particularly preferred.

The reaction of a dehydrohalogenation product according to component step B with an olefin of the general formula (III) can be carried out by initially introducing the olefin, optionally in a solvent, together with a Lewis acid and adding the reaction solution from component step B dropwise. An exothermic effect can occur here. However, the procedure can also be to add a Lewis acid to the reaction solution from component step B and to add the olefin dropwise, optionally in a solvent. An exothermic effect can also occur here. A further variant consists in bringing together the reactants (dehydrohalogenation product according to component step B, Lewis acid and olefin), optionally in a solvent, and in stirring the mixture. An exothermic effect can again occur. If a Lewis acid has already been used in component step B, its addition in component step C is superfluous.

It can sometimes be advantageous to carry out the dehydrohalogenation according to component step B already in the presence of an olefin and a Lewis acid.

The cyclo-addition of the dehydrohalogenation product present in the reaction mixture from component step B onto an olefin in the presence of a Lewis acid is a reaction which proceeds stoichiometrically. However, according to circumstances, it can be advisable to choose an amount of olefin which is slightly less than or more than the stoichiometric amount amount, e.g. about 20%.

The reaction temperature can be chosen within a wide range. Thus, the reaction can be carried out either at about $-10°$ C. or $+80°$ C. In many cases, it has been found that the cyclo-addition already begins in the temperature range from 20° to 40° C., that is to say at room temperature or slightly above, which is easy to control industrially. A reaction time of about 0.5 to 24 hours is sufficient for complete conversion.

Suitable olefins of the general formula (III) are, for example, ethylene, cyclohexene, cyclopentene, cyclobutene, propene, 1-decene, vinylene carbonate, vinyl acetate, isoprene, 3,3-dimethylcyclopropene, methyl vinyl ether, cyclooctene, penta-1,3-diene, 4-methylpenta-1,3-diene, 2,5-dimethylhexa-2,4-diene, cyclododecene, N-vinylpyrrolidone, sorbic acid ethyl ester, hexa-1,5-diene, 2,2-dimethyldioxole, dicyclopentadiene, indene, 3,3-dimethyl-butene, methylene-cyclopropane, methylenecyclobutane, styrene, methylenecyclohexane, cycloocta-1,5-diene, 1-chlorobuta-1,3-diene, 2-chlorobuta-1,3-diene, 1,1-difluorobuta-1,3-diene, 1,1,2-trifluorobuta-1,3-diene, 1,1,2-trichlorobuta-1,3-diene, 1,1-dichlorobuta-1,3-diene, 1,1-dichloro-2-fluorobuta-1,3-diene, 1,1-dichloro-2-methylbuta-1,3-diene, 1,1-dichloro-2-ethylbuta-1,3-diene, 1,1-dichloro-3-methylbuta-1,3-diene, 1,1,2-trifluoro-3-methylbuta-1,3-diene, 1,1,2-trichloro-3-methylbuta-1,3-diene, 1,1-dicyanobuta-1,3-diene, 1,1-dicyano-2-methyl-buta-1,3-diene, 1,1-difluoro-2-chlorobuta-1,3-diene, 1,1,2-trichloro-3-cyanobuta-1,3-diene, 1,1-dichloro-2-bromobuta-1,3-diene, 2-chloro-3-methylbuta-1,3-diene, 1,2-dichlorobuta-1,3-diene, 1,2-dibromobuta-1,3-diene, 1,1-dibromobuta-1,3-diene, 1,1-dibromo-2-fluoro-buta-1,3-diene, 1,1-dibromo-2-chloro-buta-1,3-diene, 1,1-dichloropenta-1,3-diene, 1,1-dichloro-hexa-1,3-diene, 1,1,2-trichloro-penta-1,3-diene, 1,1-dichloro-3-methylpenta-1,3-diene, 1,1,2-trichloro-3-methylpenta-1,3-diene, 1,1-dichloro-hepta-1,3-diene, 1,1,2-trichloro-hepta-1,3-diene, 1,1-dichloro-octa-1,3-diene, 1,1-dichloro-nona-1,3-diene, 1,1-dibromo-penta-1,3-diene, 1-acetoxy-2-chloro-buta-1,3-diene, 1,1-bis-trifluoromethyl-buta-1,3-diene, 2-methanesulphonyl-buta-1,3-diene, 1,1-dibromo-2-fluoro-penta-1,3-diene, 1,1-dichloro-2-fluoro-penta-1,3-diene, 1,3-dibromo-2-methyl-penta-1,3-diene, 1-($\beta,\beta$-dichlorovinyl)-cyclohex-1-ene, 1-vinyl-2-chloro-cyclohex-1-ene and 1-($\beta,\beta$-dichlorovinyl)-cyclopent-1-ene.

COMPONENT STEP D:

In component step D, the reaction mixture from component step C is hydrolyzed by adding water or an aqueous base or acid. In this procedure, the cyclobutanonimonium salt intermediately formed is converted, if appropriate by warming the solution to temperatures between about 20° and 100° C., preferably about 40° to 60° C., into the cyclobutanone of the general formula (I), which in each case is separated off, either directly or after steam distillation, by extraction with an organic solvent, such as, for example, toluene, dibutyl ether, chlorobenzene or methylene chloride.

The product can be obtained in an analytically pure form, for characterization, by fractional distillation, optionally under reduced pressure, and/or crystallization. In many cases, purification is superfluous and the crude cyclobutanone can be employed for further reactions.

Some of the cyclobutanones of the general formula (I), which are readily available by the process according to the invention, are valuable intermediates in the production of various plant protection agents. For example, the 2,2-dimethyl-3-halogenovinyl-substituted cyclobutanones can be halogenated in the $\alpha$-position relative to the carbonyl group and the products can then be converted directly into the biologically active insecticides of the pyrethrum type, for example Permethrin (the m-phenoxybenzyl ester of 2,2-dimethyl-3-($\beta,\beta$-dichlorovinyl)-cyclopropanecarboxylic acid) (see U.S. Patent Application Ser. No. 820,500, filed July 29, 1977, now pending.

The examples which follow illustrate the process according to the invention without indicating a limitation with regard to its applicability.

EXAMPLE 1

Preparation of the amide chloride of isobutyric acid dimethylamide.

A solution of 345.0 g (3.0 mols) of isobutyric acid dimethylamide in 2,000 ml of methylene chloride was put into a stirred vessel, provided with a stirrer, reflux condenser, dropping funnel and gas inlet tube, and 330.0 g (3.3 mols) of phosgene were passed in at 0° C., while cooling and stirring. The solution was allowed to warm to 20°–25° C. and, after standing overnight (15 hours), unreacted phosgene was distilled off, together with about ⅓ of the methylene chloride used as the solvent. The residue was diluted to 2,100 ml by adding methylene chloride.

EXAMPLE 2

Preparation of 2,2-dimethyl-3-($\alpha,\beta,\beta$-trichlorovinyl)-cyclobutanone.

50.0 g (0.5 mol) of triethylamine in 100 ml of methylene chloride were added dropwise to 350 ml of the solution, prepared according to Example 1, of the amide chloride of isobutyric acid dimethylamide in methylene chloride at 20° C., while cooling and stirring, and the mixture was then heated to reflux for 1 hour. Thereafter, 75.0 g (0.55 mol) of zinc chloride were added at 10° C. and 79.0 g (0.5 mol) of 1,1,2-trichlorobutadiene were added dropwise to the reaction solution in the course of 60 minutes. After heating the mixture for 5 hours under reflux, 400 ml of water were added and the mixture was stirred overnight (15 hours). Separating the phases, drying the organic phase over sodium sulphate and subjecting it to fractional distillation gave 10.5 g of 1,1,2-trichlorobutadiene, 11.5 g of isobutyric acid dimethylamide and 66.8 g (59%, relative to isobutyric acid dimethylamide employed) of the ketone of boiling point 112°–117° C./10 mm Hg; $n_D^{20} = 1.509$.

EXAMPLE 3

Preparation of 2,2-dimethyl-3-($\alpha,\beta,\beta$-trichlorovinyl)-cyclobutanone.

50.0 g (0.5 mol) of triethylamine in 100 ml of methylene chloride were added dropwise to 350 ml of the solution, prepared according to Example 1, of the amide chloride of isobutyric acid dimethylamide in methylene chloride at 20° C., while cooling, and the mixture was then heated to reflux for 1 hour. Thereafter, 79.0 g (0.5 mol) of 1,1,2-trichlorobutadiene were added and then 75.0 g (0.55 mol) of zinc chloride were added incrementally at 10° C., while cooling. After heating the mixture for 5 hours under reflux, it was worked up according to Example 2 to give 6.3 g of 1,1,2-trichlorobutadiene, 7.6 g of isobutyric acid dimethylamide and 70.7 g (62%, relative to isobutyric acid dimethylamide employed) of the ketone of boiling point 117°–122° C./14–15 mm Hg; $n_D^{20} = 1.509$.

EXAMPLE 4

Preparation of 2,2-dimethyl-3-($\alpha,\beta,\beta$-trichlorovinyl)-cyclobutanone.

75.0 g (0.55 mol) of zinc chloride were added to 350 ml of the solution, prepared according to Example 1, of the amide chloride of isobutyric acid dimethylamide in methylene chloride at 0° C., while cooling and stirring, and 50.0 g (0.5 mol) of triethylamine in 100 ml of methylene chloride were then added dropwise. After warming the mixture to 20°–25° C., it was heated to reflux for 1 hour and 79.0 g (0.5 mol) of 1,1,2-trichlorobutadiene were then added dropwise at 20° C. After heating the mixture for 5 hours under reflux, it was worked up according to Example 2 to give 7.2 g of 1,1,2-trichlorobutadiene, 6.3 g of isobutyric acid dimethylamide and 62.3 g (55%, relative to isobutyric acid dimethylamide employed) of the ketone of boiling point 114°–118° C./12 mm Hg; $n_D^{20} = 1.510$.

EXAMPLE 5

Preparation of 2,2-dimethyl-3-vinyl-cyclobutanone.

75.0 g (0.55 mol) of zinc chloride were added to 350 ml of the solution, prepared according to Example 1, of the amide chloride of isobutyric acid dimethylamide in methylene chloride at 0° C., while cooling and stirring, and 54.0 g (1.0 mol) of previously condensed butadiene were then passed in. 50.0 g (0.5 mol) of triethylamine in 100 ml of methylene chloride were then added dropwise, while cooling, and the mixture was allowed to warm to 20°–25° C., while stirring. After standing overnight (15 hours), it was heated for 2 hours under reflux, 200 ml of water were added and the mixture was stirred for 8 hours. Working up according to Example 2 gave 27.1 g (44%, relative to isobutyric acid dimethylamide employed) of the ketone of boiling point 89°–91° C./100 mm Hg; $n_D^{20} = 1.4454$.

EXAMPLE 6

Preparation of 2,2-dimethyl-3-($\beta$-chlorovinyl)-cyclobutanone.

44.25 g (0.5 mol) of 1-chlorobutadiene (isomer mixture) and then 50.0 g (0.5 mol) of triethylamine in 100 ml of methylene chloride were added to 350 ml of the solution, prepared according to Example 1, of the amide chloride of isobutyric acid dimethylamide in methylene chloride at 0° C., while cooling and stirring. After warming the mixture of 20° C., 75.0 g (0.55 mol) of zinc chloride were added incrementally, while cooling, and the mixture was then heated to reflux for 6 hours. After adding 250 ml of water and working up in the customary manner, 54.2 g (68%, relative to isobutyric acid dimethylamide employed) of the ketone of boiling point 81°–85° C./11–12 mm Hg ($n_D^{20} = 1.4759$) were obtained.

EXAMPLE 7

Preparation of 2,2-dimethyl-3-isopropenylcyclobutanone.

34.0 g (0.5 mol) of isoprene and then, at 0°–10° C., 75.0 g (0.55 mol) of zinc chloride were added to 350 ml of the solution, prepared according to Example 1, of the amide chloride is isobutyric acid dimethylamide in methylene chloride, while cooling and stirring. Thereafter, 50.0 g (0.5 mol) of triethylamine were added dropwise at the same temperature and, after warming to 20°–25° C., the mixture was heated to reflux and worked up according to Example 2. This gave 40.4 g (58%, relative to isobutyric acid dimethylamide employed) of the ketone of boiling point 109°–110° C./100 mm Hg and $n_D^{20}$ of 1.4518 (contaminated to the extent of about 10% by 2,2,3-trimethyl-3-vinyl-cyclobutanone).

EXAMPLE 8

Preparation of 2,2-dimethyl-3-($\beta,\beta$-dichlorovinyl)-cyclobutanone.

50.0 g (0.5 mol) of phosgene were added to a solution of 57.5 g (0.5 mol) of isobutyric acid dimethylamide in 300 ml of methylene chloride at 0° C., while stirring. The solution was allowed to warm to 20°–25° C., about 100 ml of methylene chloride were distilled off, together with unreacted phosgene, and 50.0 g (0.5 mol) of triethylamine in about 100 ml of methylene chloride were then added dropwise, while stirring and cooling. After heating the mixture to the reflux for 1 hour, it was cooled and 75.0 g (0.55 mol) of zinc chloride were added at 10°–20° C. 61.5 g (0.5 mol) of 1,1-dichlorobutadiene in 80 ml of methylene chloride were then added dropwise so that the solution simmered. The mixture was heated to the reflux for 5 hours, 400 ml of water were added at 20° C. and the mixture was stirred overnight (15 hours). Separating the phases and washing and drying the organic phase gave, after fractional distillation, 56.7 g (59%, relative to isobutyric acid dimethylamide employed, or 71%, relative to 1,1-dichlorobutadiene converted) of 2,2-dimethyl-3-($\beta,\beta$-dichlorovinyl)-cyclobutanone of boiling point 106°–110° C./13–14 mm Hg; $n_D^{20} = 1.4928$.

EXAMPLE 9

Preparation of 2,2-dimethylcyclobutanone.

50.0 g (0.5 mol) of triethylamine in 100 ml of methylene chloride were added dropwise to 350 ml of the solution, prepared according to Example 1, of the amide chloride of isobutyric acid diemthylamide at 15° C., while stirring. The mixture was heated to reflux for 1 hour and cooled and 75.0 g (0.55 mol) of zinc chloride were added. Ethylene, which had previously flowed through a drying tower charged with calcium chloride, was passed into the reaction solution at −10° C., while stirring, and the mixture was allowed to warm to 20°–25° C. While passing further ethylene in, the reaction solution was heated to the reflux for 4 hours, 250 ml of water were added at 20° C. and the mixture was stirred for a further 15 hours. Saturation of the aqueous phase with sodium chloride, exhaustive extraction with methylene chloride, drying the organic phase with sodium sulphate and evaporation of the solvent, gave about 80.0 g of crude ketone which was subjected to fractional distillation. Yield: 33.0 g (67.2%) of ketone of boiling point 56°–59° C./100 mm Hg; $n_D^{20}=1.4156$.

EXAMPLE 10

Preparation of 3-($\beta,\beta$-dichlorovinyl)-spiro[3,5]nonan-1-one.

55.0 g (0.55 mol) of phosgene were passed into a solution of 77.5 g (0.5 mol) of cyclohexanecarboxylic acid dimethylamide and 300 ml of chlorobenzene at 20°C. After stirring the mixture for 5 hours at 30°–40° C., unreacted phosgene was stripped off under reduced pressure and 55.0 g (0.55 mol) of triethylamine were then added dropwise at 20°C. The mixture was heated to 40°–50° C. for 1 hour and cooled, 75.0 g (0.55 mol) of zinc chloride were added at 20° C. and 61.5 g (0.5 mol) of 1,1-dichlorobutadiene in 50 ml of chlorobenzene were then added dropwise. After warming the mixture to 40°–50° C. for 6 hours, it was worked up as described in Example 8. Fractional distillation gave 69.6 g of crystals of melting point 58°–60° C. (from n-hexane).

EXAMPLE 11

Preparation of 2,2-diethyl-3-($\beta,\beta$-dichlorovinyl)-cyclobutanone.

36.6 g (0.25 mol) of diethylacetic acid dimethylamide in 70 ml of methylene chloride were added dropwise to a solution of 31.0 g (0.31 mol) of phosgene in 130 ml of methylene chloride in the course of 45 minutes at 10°–20° C., while stirring, and, after 15 hours, unreacted phosgene was removed under reduced pressure. 30.0 g (0.30 mol) of triethylamine in 100 ml of methylene chloride were added incrementally, while cooling, and the mixture was heated to reflux for 2 hours. 47.5 g (0.25 mol) of titanium tetrachloride were then added, while cooling; thereafter, 33.0 g (0.25 mol) of 1,1-dichlorobutadiene were added dropwise to the solution and the mixture was heated for 4 hours under reflux. After adding 150 ml of water and working up in the customary manner, 7.2 g of unreacted 1,1-dichlorobutadiene and 30.3 g of 2,2-diethyl-3-($\beta,\beta$-dichlorovinyl)-cyclobutanone (54%, relative to diethylacetic acid dimethylamide employed), of boiling point 130° to 133° C./15 mm Hg and $n_D^{20}$ 1.4969, were obtained.

Products of the novel process are useful as intermediates for preparation of other insecticides such as cyclopropanecarboxylic acid derivatives according to the applications referred to hereinabove.

It will be appreciated that the instant specification and examples are set forth by way of illustration and not limitation, and that various modifications and changes may be made without departing from the spirit and scope of the present invention.

What is claimed is:

1. A process for the preparation of a cyclobutanone of the formula

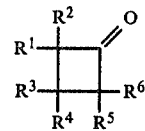

in which
R$^1$, R$^2$ and R$^3$ each independently is a hydrogen, halogen, cyano, alkoxy, alkoxycarbonyl, N,N-dialkylaminocarbonyl, alkyl, aryl, aralkyl or alkenyl radical, and
R$^4$, R$^5$ and R$^6$ each independently is hydrogen, alkyl, haloalkyl, alkenyl, haloalkenyl, halogen, cyano, aralkyl or aryl, or any two of R$^1$ to R$^6$ together with the carbon atom to which each is linked for a ring, comprising reacting an N,N-disubstituted carboxylic acid amide of the formula

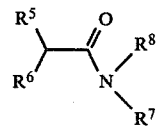

in which
R$^7$ and R$^8$ each independently is an alkyl, cycloalkyl, alkenyl, aryl or aralkyl radical or together form a ring, with an inorganic acid halide, then reacting the reaction mixture with a Lewis acid, then with a tertiary amine, and then with an olefin of the formula

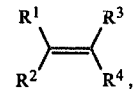

and subsequently hydrolyzing the mass.

2. A process for the preparation of a cyclobutanone of the formula

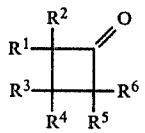

in which
R$^1$, R$^2$ and R$^3$ each independently is a hydrogen, halogen, cyano, alkoxy, alkoxycarbonyl, N,N-dialkylaminocarbonyl, alkyl, aryl, aralkyl or alkenyl radical, and
R$^4$, R$^5$ and R$^6$ each independently is hydrogen, alkyl haloalkyl, alkenyl, haloalkenyl, halogen, cyano, aralkyl or aryl, or any two of R$^1$ to R$^6$ together with the carbon atom to which each is linked form a ring.

comprising reacting an N,N-disubstituted carboxylic acid amide of the formula

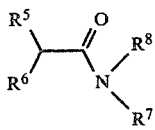

in which
R[7] and R[8] each independently is an alkyl, cycloalkyl, alkenyl, aryl or aralkyl radical or together form a ring, with an inorganic acid halide, then reacting the reaction mixture with an amine, then in the presence of a Lewis acid with an olefin of the formula

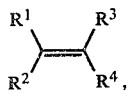

and subsequently hydrolyzing the mass.

3. A process according to claim 1 or 2, in which the reaction product of the carboxylic acid amide and inorganic acid halide is first dehydrohalogenated with the tertiary amine, the Lewis acid is then added, the product is reacted with the olefin, and then hydrolyzed.

4. A process according to claim 1 or 2, in which the Lewis acid is first added to the reaction product of the carboxylic acid amide with the inorganic acid halide, the tertiary amine and thereafter the olefin are added and the mixture is allowed to react, and is then hydrolyzed.

5. A process according to claim 1 or 2, in which the amide is a dimethylamide.

6. A process according to claim 1 or 2, in which the amide is an amide of isobutyric acid, isovaleric acid, butyric acid, caproic acid, isovaleric acid, chloroacetic acid, phenylacetic acid, α-methylbutyric acid, adipic acid, adipic acid monoethyl ester, β,β-dimethylbutyric acid, cyclohexanecarboxylic acid, cyclohexylacetic acid, cyclobutylacetic acid, cyclopentanecarboxylic acid, cyclobutanecarboxylic acid or ω-chlorocaproic acid, 2-phenylbutyric acid, 2-phenylpropionic acid, 2-ethylbutyric acid.

7. A process according to claim 1 or 2, in which the inorganic acid halide is a chloride.

8. A process according to claim 1 or 2, in which the acid halide is thionyl chloride, phosgene, phosphorus pentachloride, thionyl bromide or phosphorus trichloride.

9. A process according to claim 1 or 2, in which the Lewis acid is zinc chloride, titanium tetrachloride, aluminum chloride, zinc bromide, iron (III) chloride, tin (II) chloride or tin (IV) chloride.

10. A process according to claim 1 or 2, in which the tertiary amine is trimethylamine, triethylamine, dimethylaniline, pyridine, quinoline, tributylamine, dicyclohexylmethylamine or dimethylbenzylamine.

11. A process according to claim 1 or 2, in which the olefin is a butadiene.

12. A process according to claim 1 or 2, in which isobutyric acid dimethylamide is employed as the carboxylic acid amide, phosgene is employed as the inorganic acid halide, triethylamine is employed as the tertiary amine and zinc chloride or titanium tetrachloride is employed as the Lewis acid.

13. A process according to claim 1 or 2, in which the reaction between the amide and the inorganic acid halide is effected at about $-10°$ to $+100°$ C. and about 1 to 1.3 moles of the inorganic acid halide are employed per mol of the amide.

14. A process according to claim 1 or 2, in which the dehydrohalogenation with the tertiary amine is effected at about $-30°$ C. to $+100°$ C. and the tertiary amine is employed in at least the stoichiometric amount.

15. A process according to claim 1 or 2, in which the reaction with the olefin is effected at about $-10°$ C. to $+80°$ C.

16. A process according to claim 1 or 2, in which the hydrolysis is effected by addition of water, aqueous acid or aqueous base and the cyclobutanonimonium salt immediately formed is converted to the corresponding cyclobutanone by heating the solution to about 20° to 100° C.

17. A process according to claim 6, in which the acid halide is thionyl chloride, phosgene, phosphorus pentachloride, thionyl bromide or phosphorus trichloride, the Lewis acid is zinc chloride, titanium tetrachloride, aluminum chloride, zinc bromide, iron (III) chloride, tin (II) chloride or tin (IV) chloride, the tertiary amine is trimethylamine, triethylamine, dimethylaniline, pyridine, quinoline, tributylamine, dicyclohexylmethylamine or dimethylbenzylamine and the olefin is a butadiene, the reaction between the amide and the inorganic acid halide is effected in an inert organic solvent at about 31 10° to $+40°$ C. with about 1 to 1.3 times as many moles of inorganic acid halide as amide, the dehydrohalogenation is effected with at least the stoichiometric amount of the tertiary amine at about $-20°$ to $+40°$ C., the reaction with the olefin is effected at about 20° to 40° C., and the hydrolysis is effected by addition of water, aqueous acid or aqueous base and the cyclobutanonimonium salt immediately formed is converted to the corresponding cyclobutanone by heating the solution to about 40° to 60° C.

18. A process according to claim 17, in which isobutyric acid dimethylamide is employed as the carboxylic acid amide, phosgene is employed as the inorganic acid halide, triethylamine is employed as the tertiary amine and zinc chloride or titanium tetrachloride is employed as the Lewis acid.

* * * * *